United States Patent [19]

Ehr et al.

[11] Patent Number: 5,441,104
[45] Date of Patent: Aug. 15, 1995

[54] FLUID CIRCULATOR AND TEMPERATURE REGULATOR

[75] Inventors: Timothy G. J. Ehr, Menomonee Falls; Michael E. Hansen, Waukesha; Scott T. Breyer, Oconomowoc, all of Wis.

[73] Assignee: Fotodyne Incorporated, Hartland, Wis.

[21] Appl. No.: 181,579

[22] Filed: Jan. 13, 1994

Related U.S. Application Data

[63] Continuation-in-part of Ser. No. 820,529, Jan. 14, 1992, Pat. No. 5,323,846.

[51] Int. Cl.⁶ .................................. F28D 15/00
[52] U.S. Cl. ..................... 165/104.32; 204/299 R
[58] Field of Search ............... 165/104.32, 95, 71; 204/299 R

[56] References Cited

U.S. PATENT DOCUMENTS

| 2,041,241 | 5/1936 | Goldfield | 165/104.32 |
| 3,989,102 | 11/1976 | Jaster et al. | 165/104.32 |
| 4,592,418 | 6/1986 | Cadars | 165/104.32 |
| 4,612,106 | 9/1986 | Kromer et al. | 204/299 |
| 4,909,312 | 3/1990 | Biedenbach et al. | 165/104.32 |
| 5,158,661 | 10/1992 | Hansen | 204/299 R |

FOREIGN PATENT DOCUMENTS

| 287513 | 10/1988 | European Pat. Off. |
| 636525 | 5/1950 | United Kingdom |
| 952195 | 3/1964 | United Kingdom |
| 2236842 | 4/1991 | United Kingdom |

Primary Examiner—John Rivell
Assistant Examiner—Christopher Atkinson
Attorney, Agent, or Firm—Michael, Best & Friedrich

[57] ABSTRACT

A fluid circulator and temperature regulator apparatus for use in an electrophoresis process with a sequencing cell including a cooling jacket having an inlet and an outlet, the apparatus comprising an inlet adapted to be connected to the cooling jacket outlet, an outlet adapted to be connected to the cooling jacket inlet, a reservoir having an inlet, an outlet and a vent, a heat exchanger having an inlet and an outlet, a pump having an inlet and an outlet, the reservoir, the heat exchanger and the pump being fluidly connected in a flow path having an upstream end and a downstream end, with the reservoir being downstream of the pump, and valves operable in a first mode for connecting the downstream end of the flow path with the outlet port and for connecting the inlet port with the upstream end of the flow path, and operable in a second mode for connecting the downstream end of the flow path with the upstream end the flow path internally of the apparatus such that fluid flows from the downstream end of the flow path to the upstream end of the flow path without flowing to the outlet.

4 Claims, 7 Drawing Sheets

Fig. 1

FLUID CIRCULATOR AND TEMPERATURE REGULATOR

RELATED APPLICATION

This is a continuation-in-part of Ser. No. 820,529, filed Jan. 14, 1992, now U.S. Pat No. 5,323,846.

FIELD OF THE INVENTION

The invention relates to apparatus used in gel electrophoretic separations of DNA molecules, protein and other charged molecules. This is commonly referred to as DNA sequencing apparatus or electrophoresis apparatus. More particularly, the invention relates to devices employed with electrophoresis apparatus to circulate fluids through a sequencing cell and to regulate the temperature of such fluids.

BACKGROUND OF THE INVENTION

A known electrophoresis apparatus includes a sequencing cell with a cooling jacket, a power supply, and a device for circulating coolant through the cooling jacket. This device includes a temperature-controlled water bath and a pump for circulating water through the cooling jacket.

Most temperature controlling baths associated with laboratory equipment are structured to circulate a fluid (typically water) within the confines of a bath. The circulator moves the working fluid past the heating and/or cooling coils and achieves a generally uniform bath temperature.

Additionally, circulation units designed to pass thermostatically controlled liquid through jacketed equipment and closed vessels are common in the art. Such devices are often substantially identical to the above baths with the addition of circulating ports. A pump is generally, but not always, included in the apparatus to perform the circulating function. Some provide pressure or suction capabilities to the external equipment to be cooled. Such devices, like the baths above, use compressor-based refrigeration to achieve temperatures below ambient.

With known circulation units it is necessary to disconnect the unit from the cell in order to drain the cell.

SUMMARY OF THE INVENTION

The invention provides a thermal regulator that circulates cooling water or fluid through a sequencing cell and that regulates the temperature of the cooling fluid. The thermal regulator includes a microprocessor-controlled liquid-to-air heat exchanger. Heating and cooling is done with thermoelectric modules. Pumping of fluid is by an oscillating pump. Path of fluid flow is controlled by two solenoid valves. Fluid is contained in a reservoir internal to the unit.

The temperature of the liquid can preferably be set from 20.0° to 50.0° C. The microprocessor maintains the fluid at the set temperature by reading the temperature of the fluid (by thermistor) and controlling both the direction and level of current to the thermoelectrics. The microprocessor utilizes an algorithm (PID LOOP) to compare the temperature set point to the actual fluid temperature and determine a current level and direction for the thermoelectrics. Actual temperature of the fluid can also be displayed on the front panel.

Fluid flow rate is controlled by adjusting the speed of the fluid pump. The microprocessor controls the speed of the pump by controlling the phase angle of a half-wave rectified sine wave. The flow rate of the pump is user-programmable by keys and a display on the front panel.

The thermal regulator preferably has inlet and outlet ports on the front of the unit and fill and overflow ports on the back of the unit. The path of fluid flow is controlled by two solenoid valves. There are three basic paths: bypass (degas); circulate; and reservoir.

In bypass mode the unit is only circulating fluid internal to the unit. The reason for this is to elevate the temperature of the fluid so that gas can escape the fluid before the fluid is fed to the electrophoresis cell.

In circulate mode, the fluid is circulated externally to the electrophoresis cell. An alternative use for this mode is to empty the reservoir of fluid. This is done by disconnecting the cell from the inlet and outlet ports, connecting a tube to the outlet port, and blocking the overflow port. Fluid can then be removed from the unit. The reservoir would be emptied for cleaning or transportation.

In reservoir mode, fluid is removed from the cell (replaced with air) and returned to the reservoir. An alternative use for this mode is to fill the reservoir. To fill the reservoir, a first tube is connected between the inlet and outlet ports and a second tube is connected to the fill port. Water (fluid) is drawn into the unit by the second tube and is circulated through the cell and into the reservoir. Air is vented from the top of the reservoir through the overflow port.

The fluid path or mode is user-programmable by keys and a display on the front panel. The microprocessor controls the solenoids.

An interlock connector is controlled by the microprocessor. The interlock connector is a switch that is normally closed when the thermal regulator is in run-cell mode and that is open when the regulator is in any other mode. The interlock connector or switch is connected to the 10 KV power supply. If the interlock switch is closed, the 10 KV power supply will recognize this and output its voltage. If the switch is open, no voltage is output to the sequencing cell. Thus, the cell cannot be powered unless the thermal regulator is in run-cell mode. The interlock thereby prevents the user from ruining the run by forgetting to switch the thermal regulator to run-cell mode.

Two limit switches are located in the reservoir, one a low-limit switch and the other a high-limit switch. The microprocessor will recognize the high limit and shut off the pump. This could only happen when the user is filling the reservoir. If fluid flow does not shut off, the reservoir will overflow and water will exit the reservoir through the vent. When the low limit is recognized by the microprocessor, it disables the interlock switch (and thereby shuts off the power supply) and shuts off the pump. If the reservoir were emptied of fluid and the pump continued to operate, air would enter the cell and possibly ruin the run.

An advantage of the thermal regulator is that the degas and empty-cell modes are operable while the regulator is connected to the sequencing cell. The degas mode also operates while the regulator is disconnected from the cell.

Another advantage of the thermal regulator is that fluid is sucked from the cell rather than being pumped under pressure to the cell. This substantially eliminates the risk water leaking out of the cell and presenting a risk of electric shock. Additionally, a kink in either of the tubes running between the cell and the temperature regulator will not result in water leaking from the cell.

Another advantage of the thermal regulator is that cooling fluid is pumped out of the cooling jacket rather than, as with known systems, simply flowing out due to gravity when the fluid circulator is disconnected from the cell.

Before one embodiment of the invention is explained in detail, it is to be understood that the invention is not limited in its application to the details of the construction and the arrangements of components set forth in the following description or illustrated in the drawings. The invention is capable of other embodiments and of being practiced or being carried out in various ways. Also, it is to be understood that the phraseology and terminology used herein is for the purpose of description and should not be regarded as limiting.

DESCRIPTION OF THE PREFERRED EMBODIMENT

Figure 1:
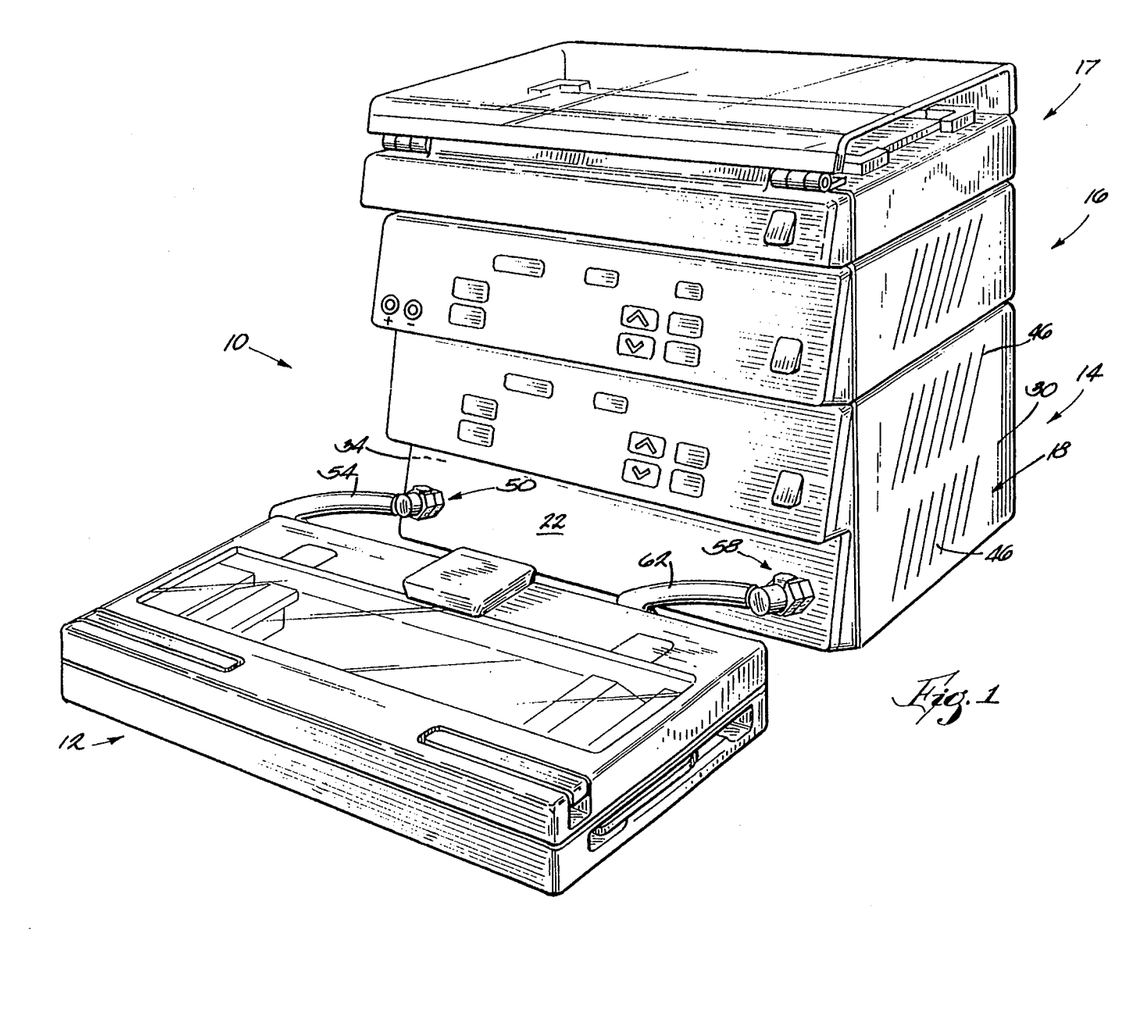
FIG. 1 is a perspective view of an electrophoresis apparatus embodying the invention and including a fluid circulator and temperature regulator.

An electrophoresis apparatus 10 embodying the invention is illustrated in the drawings. As shown in FIG. 1, the apparatus 10 comprises, generally, a sequencing cell 12, a fluid circulator and temperature regulator 14, also known as a thermal regulator, a power supply 16, and a gel dryer 17. The sequencing cell 12 is preferably the same as is described in U.S. Pat. No. 5,242,568, which issued Sep. 7, 1993, which is assigned to the assignee hereof, and which is incorporated herein by reference. The cell 12 includes a cooling jacket (not shown) having an inlet and on outlet. The power supply 16 and gel dryer 7 are conventional and will not be described in greater detail.

Except as described herein, the fluid circulator 14 is identical to the fluid circulator disclosed in above-mentioned U.S. Ser. No. 820,529, which is incorporated herein by reference, and common elements have been given the same reference numerals. The fluid circulator 14 comprises (see FIG. 1) a generally rectangular housing 18 including a front panel 22, a rear panel (not shown), and opposite side walls 30 and 34. The side walls 30 and 34 have therein vent openings 46. The front panel 22 has thereon an outlet connector or port 50 which, in FIG. 1, is connected to the cooling jacket inlet via a flexible conduit 54. The front panel 22 also has thereon an inlet connector or port 58 which, in FIG. 1, is connected to the cooling jacket outlet via a flexible conduit 62. Alternatively, the connectors 50 and 58 can be connected to each other by either conduit 54 or conduit 62. Each of the connectors 50 and 58 is valved such that fluid flow through the connector is prevented when a conduit is not in communication with the connector. Such connectors are known in the art and need not be described in greater detail. The rear panel has therein (see FIG. 2) an overflow port 66 and a fill port 70. The ports 66 and 70 are not valved.

The fluid circulator 14 also comprises (see FIG. 2), within the housing 18, a reservoir 74 having a cooling fluid inlet 78, a cooling fluid outlet 82, and a vent opening 86. Also within the housing 18 is a heat exchanger 94 having a cooling fluid inlet 98 and a cooling fluid outlet 102. The heat exchanger 94 can both cool and heat fluid and is preferably the same as is described in U.S. Pat. No. 5,158,661, which issued Oct. 27, 1992, which is assigned to the assignee hereof, and which is incorporated herein by reference.

Figure 2:
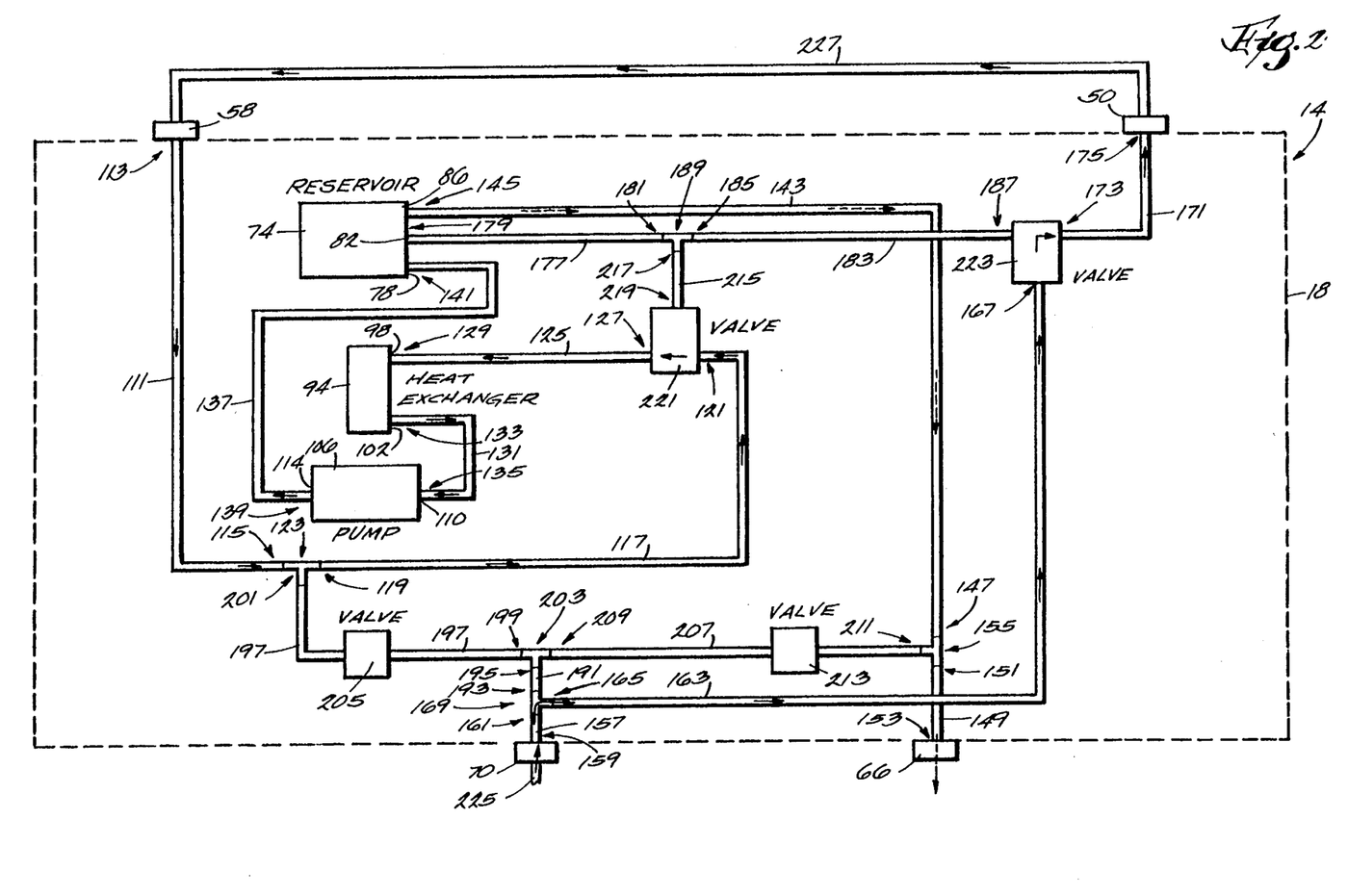
FIG. 2 is a schematic view of the internal components of the fluid circulator and temperature regulator, showing operation of the fluid circulator and temperature regulator to fill the reservoir.

The fluid circulator 14 also comprises, within the housing 18, a fluid pump 106 having an inlet 110 and an outlet 114. The pump 106 is capable of pumping both air and cooling fluid. Preferably, the pump 106 is a model 14825-641 manufactured by Gorman Rupp Company of Bellville, Ohio.

The fluid circulator 14 further comprises a tube 111 having a first end 113 communicating with the inlet port 58. The first end 113 of the tube 111 is thus adapted to communicate with the cooling jacket outlet. The tube 111 also has a second end 115. A tube 117 has a first end 119 communicating with the second end 115 of the tube 111 and has a second end 121. The tube ends 115 and 119 are preferably connected by two legs of a conventional T-connector 123 having a third leg connected to a tube described below. A tube 125 has a first end 127 and has a second end 129 communicating with the heat exchanger inlet 98. A tube 131 has a first end 133 communicating with the heat exchanger outlet 102 and has a second end 135 communicating with the pump inlet 110. A tube 137 has a first end 139 communicating with the pump outlet 114 and has a second end 141 communicating with the reservoir inlet 78.

The fluid circulator 14 further comprises a tube 143 having a first end 145 communicating with the reservoir vent 86 and having a second end 147. A tube 149 has a first end 151 communicating with the tube end 147 and has a second end 153 communicating with the overflow port 66. The tube ends 147 and 151 are preferably connected by two legs of a conventional T-connector 155 having a third leg connected to a tube described below. A tube 157 has a first end 159 communicating with the fill port 70 and has a second end 161. A tube 163 has a first end 165 communicating with the tube end 161 and has a second end 167. The tube ends 161 and 165 are preferably connected by two legs of a conventional T-connector 169 having a third leg connected to a tube described below. A tube 171 has a first end 173 and has a second end 175 communicating with the outlet port 50. The tube end 175 is thus adapted to communicate with the cooling jacket inlet.

The fluid circulator 14 further comprises a tube 177 having a first end 179 communicating with the reservoir outlet 82 and having a second end 181. A tube 183 has a first end 185 communicating with the tube end 181 and has a second end 187. The tube ends 181 and 185 are preferably connected by two legs of a conventional T-connector 189 having a third leg connected to a tube described below. A tube 191 has a first end 193 and has a second end 195. The tube end 193 is connected to the third leg of the T-connector 169 and thus communicates with the tube ends 161 and 165.

A tube 197 has a first end 199 communicating with the tube end 195 and has a second end 201 communicating with the third leg of the T-connector 123. The tube end 201 thus communicates with the tube ends 115 and 119. The tube ends 195 and 199 are connected by two legs of a conventional T-connector 203 having a third leg connected to a tube described below. The tube 197 has therein a check valve 205 that permits fluid flow in the direction from the tube end 199 to the tube end 201 and prevents fluid flow in the direction from the tube end 201 to the tube end 199. A tube 207 has a first end 209 communicating with the third leg of the T-connector 203. The tube end 209 thus communicates with the tube ends 195 and 199. The tube 207 also has a second end 211 communicating with the third leg of the T-connector 155. The tube end 211 thus communicates with the tube ends 147 and 151. The tube 207 has therein a check valve or pressure relief valve 213 which prevents fluid flow in the direction from the tube end 209 to the tube end 211 and permits fluid flow in the direction from the tube end 211 to the tube end 209 when the fluid pressure in the tube 207 on the right side of the valve 213 exceeds a predetermined value. This predetermined value is preferably is 1.5 psi. A tube 215 has a first end 217 communicating with the third leg of the connector 189. The tube end 217 thus communicates with the tube ends 181 and 185. The tube 215 also has a second end 219.

The tube ends 121, 127 and 219 are connected to a valve 221 operable between a first state in which the tube ends 121 and 127 are connected and the tube end 219 is blocked and a second state in which the tube ends 219 and 127 are connected and the tube end 121 is blocked. While various suitable valves can be employed, in the illustrated construction, the valve 221 is a conventional solenoid valve. The valve is preferably a model 651148 manufactured by KIP Incorporated of Farmington, Conn.

The tube ends 167, 173 and 187 are connected to a valve 223 operable between a first state in which the tube ends 167 and 173 are connected and the tube end 187 is blocked and a second state in which the tube ends 173 and 187 are connected and the tube end 167 is blocked. While various suitable valves can be employed, in the illustrated construction, the valve 223 is a conventional solenoid valve that is preferably identical to the valve 221.

The fluid circulator 14 is operable in three different modes: 1) reservoir mode; 2) circulate mode; and 3) by-pass mode. In FIGS. 2 through 7 of the drawings, water flow is indicated by solid arrows and air flow is indicated by broken arrows.

1) Reservoir Mode.

Figure 3:
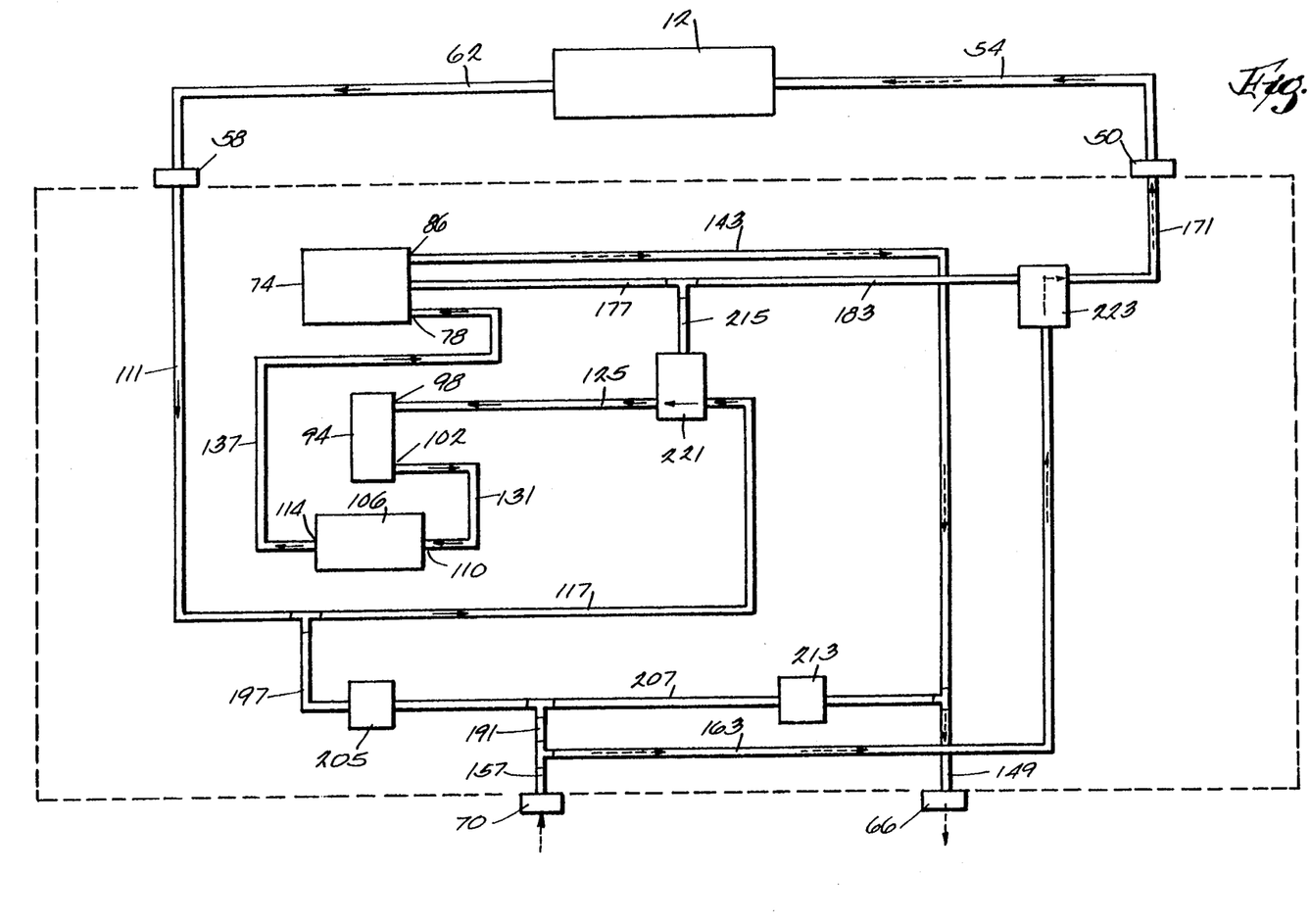
FIG. 3 is a view similar to FIG. 2 showing operation of the fluid circulator and temperature regulator to drain the cell.

In reservoir mode, the valve 221 is in its first state and the valve 223 is in its first state. The fluid circulator 14 can be operated in reservoir mode to either fill the reservoir 74 or drain the cooling jacket of the cell 12.

In order to fill the reservoir 74, as shown in FIG. 2, a tube 225 is connected between the fill port 70 and a source of cooling fluid or water, and a tube 227 is connected between the outlet port 50 and the inlet port 58. The tube 227 can be one of the tubes 54 and 62. When the pump 106 is activated, water flows through the tubes 225, 157 and 163 to the valve 223, through the tubes 171, 227, 111 and 117 to the valve 221, through the tube 125 to the heat exchanger 94, from the heat exchanger 94 to the pump 106 through the tube 131, and from the pump 106 to the reservoir inlet 78 through the tube 137. Air in the reservoir 74 is vented to the overflow port 66 through the tubes 143 and 149.

In order to drain the cooling jacket of the cell 12, as shown in FIG. 3, the tubes 54 and 62 are connected between the fluid circulator 14 and the cell 12 in the same manner as shown in FIG. 1. The tube 225 is disconnected from the fill port 70. When the pump 106 is activated, fluid flows from the cell cooling jacket through the tubes 62, 111 and 117 to the valve 221. From the valve 221, fluid flows through the tube 125 to the heat exchanger 94. Fluid flows from the heat exchanger 94 to the pump 106 through the tube 131 and flows from the pump 106 to the reservoir inlet 78 through the tube 137. Air is vented from the reservoir 74 through the tubes 143 and 149 and the overflow port 66. Air flows through the fill port 70, the tubes 157 and 163, the valve 223, and the tubes 171 and 54 to the cell cooling jacket. If the fill port 70 should somehow become blocked, the pressure relief valve 213 opens to allow air to flow through the tubes 207 and 191 to the tube 163 and then to the cell 12 as described above.

2) Circulate Mode.

Figure 4:
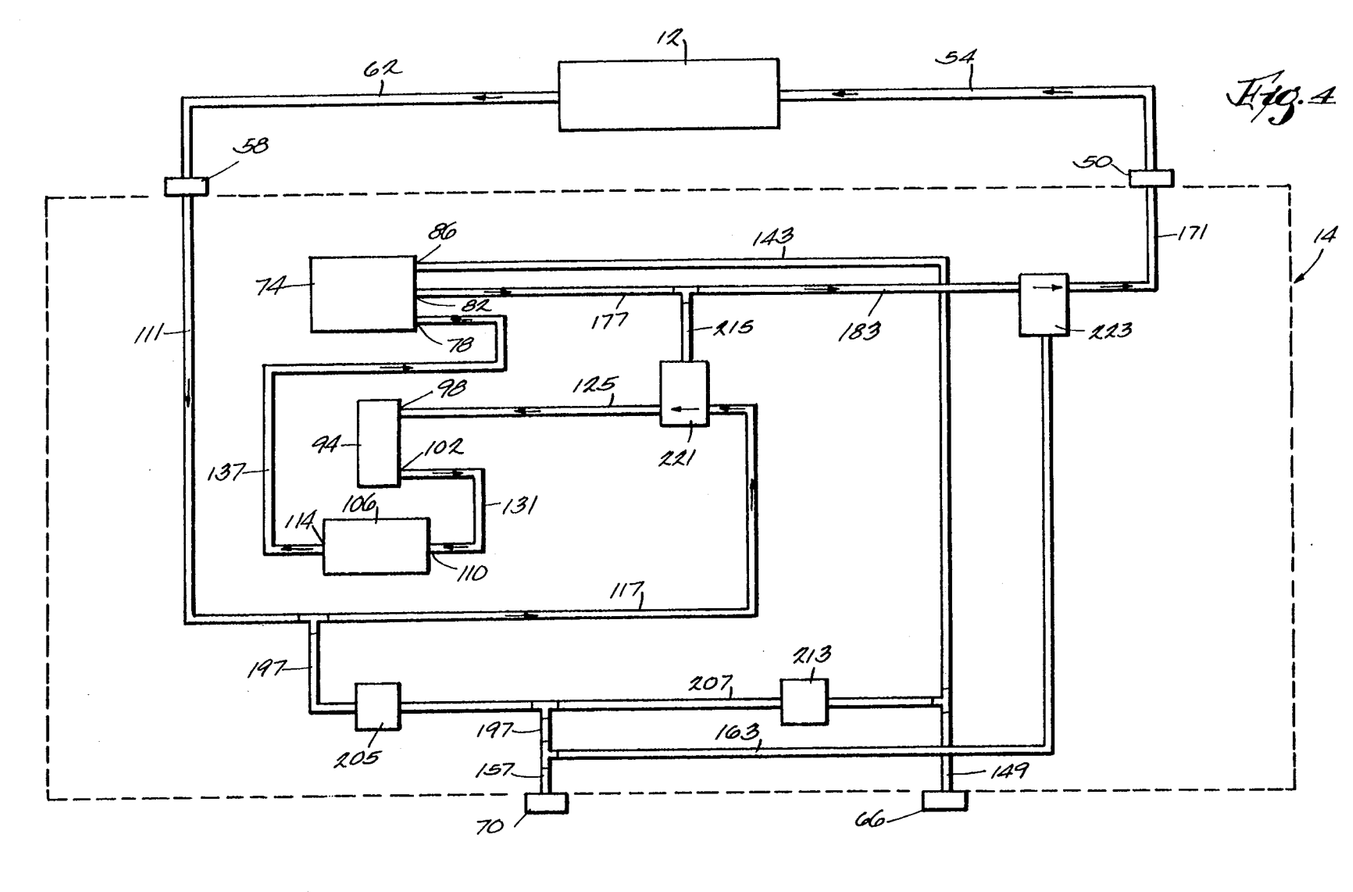
FIG. 4 is a view similar to FIG. 2 showing operation of the fluid circulator and temperature regulator to circulate cooling fluid through the cell.
Figure 6:
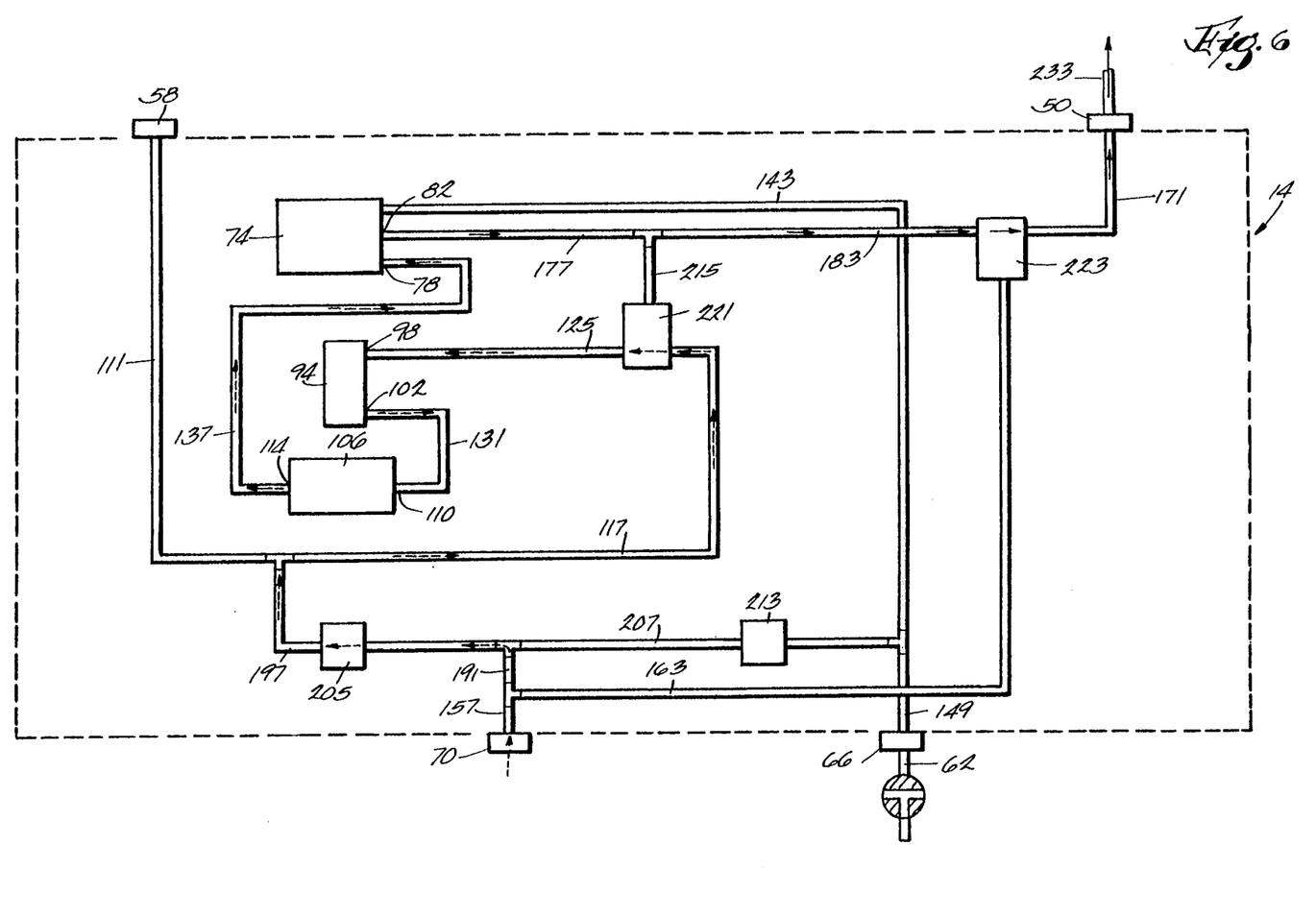
FIG. 6 is a view similar to FIG. 2 showing operation of the fluid circulator and temperature regulator to drain the reservoir.

In circulate mode, the valve 221 is in its first state and the valve 223 is in its second state. The fluid circulator 14 can be operated in circulate mode to either circulate cooling fluid through the cell 12 or empty the reservoir 74.

In order to circulate water or cooling fluid through the cell cooling jacket, as shown in FIG. 4, the tubes 54 and 62 are connected between the fluid circulator 14 and the cell 12 in the same manner as shown in FIG. 1. When the pump 106 is activated, fluid flows from the cell cooling jacket through the tubes 62, 111 and 117 to the valve 221. From the valve 221, fluid flows through the tube 125 to the heat exchanger 94. Fluid flows from the heat exchanger 94 to the pump 106 through the tube 131 and flows from the pump 106 to the reservoir inlet 78 through the tube 137. From the reservoir outlet 82, water flows through the tubes 177 and 183 to the valve 223. From the valve 223, water flows through the tubes 171 and 54 to the cooling jacket inlet.

Figure 5:
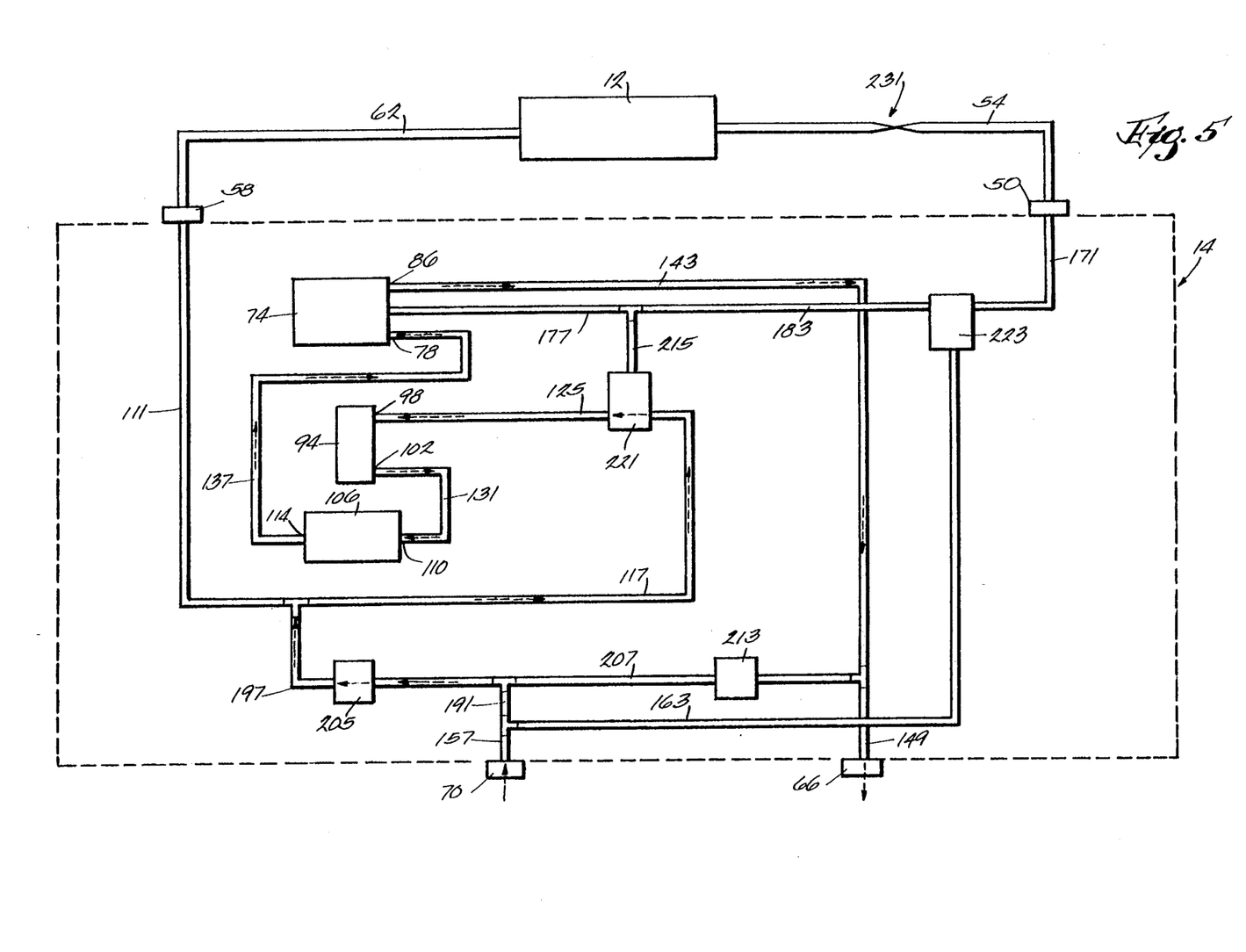
FIG. 5 is a view similar to FIG. 2 showing operation of the fluid circulator and temperature regulator when one of the tubes to the cell is kinked.

If either of the tubes 54 and 62 should become kinked or otherwise obstructed while fluid is being circulated through the cell 12, the fluid circulator 14 operates as shown in FIG. 5 in which an obstruction in tube 54 is indicated by reference numeral 231. First, it should be understood that the obstruction 231 causes water in the tubes 177, 183, 171, 54, 62 and 111 to become stationary. Because the pump 106 cannot suck water from the tube 111, the check valve 205 opens and permits air to flow through the fill port 70 and the tubes 157, 191 and 197 to the tube 117. The air then flows through the tube 117, the valve 221, the tube 125, the heat exchanger 94, the tube 131, the pump 106 and the tube 137 to the reservoir inlet 78. Air is vented from the reservoir 74 through the tubes 143 and 149 and the overflow port 66. The fluid circulator 14 can continue to operate in this manner until the obstruction 231 is removed. If the fill port 70 should somehow become blocked, the pressure relief valve 213 opens to allow air to flow through the tube 207 to the tube 197 and then to the reservoir 74 as described above.

To empty the reservoir 74, as shown in FIG. 6, the tubes 54 and 62 (shown in FIG. 1) are disconnected from the fluid circulator 14 and the overflow port 66 is closed. The overflow port 66 can be closed by connecting one end of the tube 62 (or the tube 54) to the overflow port 66 while leaving the opposite end of the tube 62 unconnected. The valve (shown schematically) in the unconnected end of the tube 62 prevents fluid flow through the tube 62 and thereby closes the overflow port 66. Also, a tube 233 is connected between the outlet port 50 and a sink or other drain. When the pump 106 is activated, the check valve 205 opens and air flows to the pump 106 through the fill port 70, the tubes 157, 191, 197, 117 and 125, the heat exchanger 94 and the tube 131. Air flows from the pump 106 to the reservoir inlet 78 through the tube 137. From the reservoir outlet 82, water flows through the tubes 177, 183, 171 and 233 to the sink. If the fill port 70 should somehow become blocked, or if tube 233 is not attached to port 50, the pressure relief valve 213 opens to allow air to flow through the tube 207 to the tube 197 and then to the reservoir 74 as described above.

3) By-pass Mode.

Figure 7:
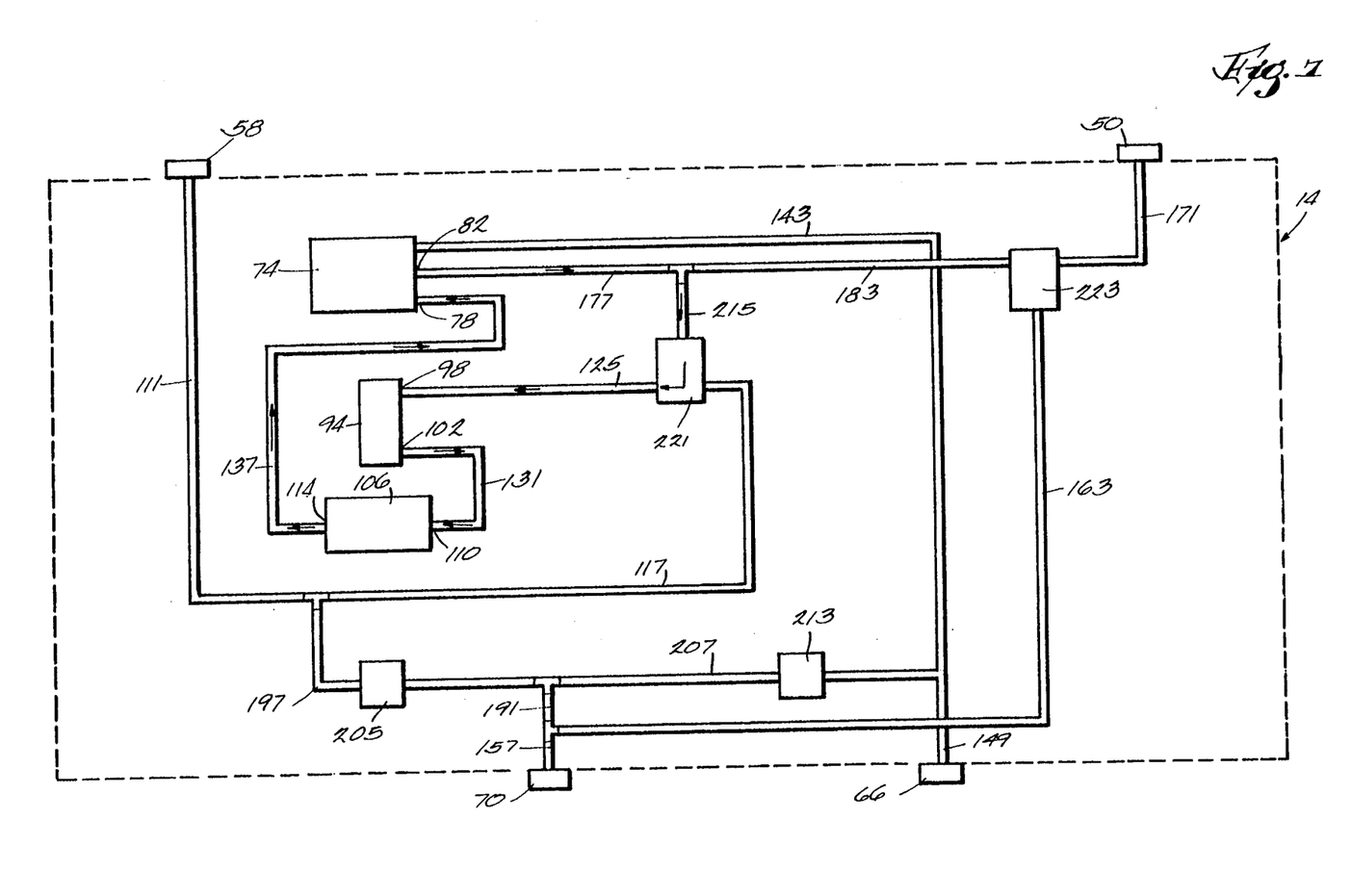
FIG. 7 is a view similar to FIG. 2 showing operation of the fluid circulator and temperature regulator to degasify fluid in the reservoir.

In by-pass mode the valve 221 is in its second state and the valve 223 is in its first state. The fluid circulator is operated in by-pass mode to degasify fluid in the reservoir As shown in FIG. 7, when the pump 106 is activated fluid flows from the pump 106 to the reservoir inlet 78 through the tube 137. Fluid flows from the reservoir outlet 82 to the heat exchanger 94 through the tubes 177 and 215, the valve 221, and the tube 125, and fluid flows from the heat exchanger 94 to the pump 106 through the tube 131. The fluid is degasified by being heated in the heat exchanger 94, after which vapor in the fluid expands and bubbles out of the fluid in the reservoir.

The circulator 14 further comprises a microprocessor (not shown) for controlling the solenoid valves 221 and 223 and the pump 106. The microprocessor is mounted inside the front panel 22 (see FIG. 1) and is connected to operating switches and readouts on the front panel 22. The operating switches allow the operator to choose the operating mode (reservoir, circulate or by-pass), to set the desired coolant temperature, and to vary pump speed. The microprocessor includes an interlock switch or connector (not shown) that is operably connected to the power supply 16. The interlock switch is normally closed when the circulator 14 is in the circulate mode so that the power supply 16 outputs voltage. The interlock switch is open when the circulator 14 is in either the reservoir or by-pass mode, so that the power supply 16 does not output voltage. As a result, the operator cannot run the cell 12 unless the circulator 14 is in the circulate mode.

Means are provided for preventing fluid flow to the cooling jacket when the volume of fluid in the reservoir 74 falls below a first predetermined level. This means preferably includes a conventional low-limit float switch (not shown) located in the reservoir 74. The switch is normally closed and opens when the fluid in the reservoir 74 falls below the first level. Opening of the switch closes or disables the interlock switch and also shuts off the pump 106. This prevents the pump 106 from pumping air to the cooling jacket and also prevents operation of the cell 12.

Means are also provided for preventing fluid flow to the reservoir 74 when the volume of fluid in the reservoir 74 reaches a predetermined second level. This means preferably includes a conventional high-limit float switch (not shown) located in the reservoir 74. The switch is normally closed and opens when the fluid level in the reservoir 74 reaches the second level. Opening of the switch shuts off the pump 106 and thereby prevents overfilling of the reservoir 74.

Referring to FIG. 2, the tubes 111 and 117 define a first conduit having a first end communicating with the inlet port 58 and having a second or downstream end, the tube 125 defines a second conduit having a first or upstream end and having a second end communicating with the heat exchanger inlet 98, the tube 131 defines a third conduit having a first end communicating with the heat exchanger outlet 102 and having a second end communicating with the pump inlet 110, the tube 137 defines a fourth conduit having a first end communicating with the pump outlet 114 and having a second end communicating with the reservoir inlet 78, the tube 177 defines a fifth conduit having a first end communicating with the reservoir outlet 82 and having a second or downstream end, the tube 171 defines a sixth conduit having a first or upstream end and having a second end communicating with the outlet port 50, and the tubes 157 and 163 define a seventh conduit having a first end communicating with the fill port 70 and having a second or downstream end. The valves 221 and 223 constitute valve means operable in a first mode (reservoir mode) for connecting the second end of first conduit (tube end 121) with the first end of the second conduit (tube end 127) and for connecting the first end of the sixth conduit (tube end 173) with the second end of the seventh conduit (tube end 167), operable in a second mode (circulate mode) for connecting the second end of the first conduit (tube end 121) with the first end of the second conduit (tube end 127) and for connecting the second end of the fifth conduit (tube end 181) with the first end of the sixth conduit (tube end 173, via tube 183), and operable in a third mode (by-pass mode) for connecting the first end of the second conduit (tube end 127) with the second end of the fifth conduit (tube end 181, via tube 215) and for connecting the first end of the sixth conduit (tube end 173) with the second end of the seventh conduit (tube end 167).

Also, the heat exchanger 94, the tube 131, the pump 106, the tube 137 and the reservoir 74 define a flow path, with the reservoir 74 being downstream of the pump 106. The valves 221 and 223 constitute valve means operable in one mode (circulate mode) for connecting the downstream end of the flow path (reservoir outlet 82) with the outlet port 50 and for connecting the inlet port 58 with the upstream end of the flow path (heat exchanger inlet 98), and operable in another mode (by-pass mode) for connecting the downstream end of the flow path with the upstream end the flow path internally of the circulator 14 such that fluid flows from the downstream end of the flow path to the upstream end of the flow path without flowing to the outlet 50.

An important feature of the circulator 14 is that the circulator 14 can circulate fluid through the cell 12, regulate fluid temperature, degasify fluid, and drain the cell cooling jacket while the circulator 14 is connected to the cooling jacket. In other words, it is not necessary to disconnect the cooling jacket from the circulator 14 in order to degasify fluid in the reservoir 74 or drain the cooling jacket. Fluid can also be degasified when the circulator 14 is not connected to the cooling jacket. Thus, the degasifying means is operable regardless of whether the circulator 14 is connected to the cooling jacket.

Various features of the invention are set forth in the following claims.

We claim:

1. A fluid circulator and temperature regulator apparatus for use in an electrophoresis process with a sequencing cell including a cooling jacket having an inlet and an outlet, said apparatus comprising an inlet port adapted to be connected to the cooling jacket outlet, an outlet port adapted to be connected to the cooling jacket inlet, a fill port, an overflow port, a reservoir having an inlet, an outlet and a vent, a heat exchanger having an inlet and an outlet, a pump having an inlet and an outlet, a first conduit having a first end communicating with said inlet port and having a second end, a second conduit having a first end and having a second end communicating with said heat exchanger inlet, a third conduit having a first end communicating with said heat exchanger outlet and having a second end communicating with said pump inlet, a fourth conduit having a first end communicating with said pump outlet and having a second end communicating with said reservoir inlet, a fifth conduit having a first end communicating with said reservoir outlet and having a second end, a sixth conduit having a first end and having a second end communicating with said outlet port, a seventh conduit having a first end communicating with said fill port and having a second end, and valve means operable in a first mode for connecting said second end of first conduit with said first end of said second conduit and for connecting said first end of said sixth conduit with second end of said seventh conduit, operable in a second mode for connecting said second end of said first conduit with said first end of said second conduit and for connecting said second end of said fifth conduit with said first end of said sixth conduit, and operable in a third mode for connecting said first end of said second conduit with said second end of said fifth conduit and for connecting said first end of said sixth conduit with said second end of said seventh conduit.

2. Apparatus as set forth in claim 1 wherein said valve means includes a first valve operable in a first state for connecting said second end of said first conduit with said first end of said second conduit and operable in a second state for connecting said second end of said fifth conduit with said first end of said second conduit, and a second valve operable in a first state for connecting said second end of said seventh conduit with said first end of said sixth conduit and operable in a second state for connecting said second end of said fifth conduit with said first end of said sixth conduit, wherein said first valve is in said first state when said apparatus is in said first and second modes and is in said second state when said apparatus is in said third mode, and wherein said second valve is in said first state when said apparatus is in said first and third modes and is in said second state when said apparatus is in said second mode.

3. A fluid circulator and temperature regulator apparatus for use in an electrophoresis process with a sequencing cell including a cooling jacket having an inlet and an outlet, said apparatus comprising an inlet port adapted to be connected to the cooling jacket outlet, an outlet port adapted to be connected to the cooling jacket inlet, a reservoir having an inlet, an outlet and a vent, a heat exchanger having an inlet and an outlet, a pump having an inlet and an outlet, said reservoir, said heat exchanger and said pump being fluidly connected in a flow path having an upstream end and a downstream end, with said reservoir being downstream of said pump, and valve means operable in a first mode for connecting said downstream end of said flow path with said outlet port and for connecting said inlet port with said upstream end of said flow path, and operable in a second mode for connecting said downstream end of said flow path with said upstream end of said flow path internally of said apparatus such that fluid flows from said downstream end of said flow path to said upstream end of said flow path without flowing to said outlet port.

4. Apparatus as set forth in claim 3 wherein said heat exchanger is upstream of said reservoir and downstream of said pump.

* * * * *